United States Patent [19]
Gordon et al.

[11] Patent Number: 5,677,197
[45] Date of Patent: Oct. 14, 1997

[54] BIOCHEMICAL ASSAY PLATE AND METHOD FOR MAKING THE SAME

[75] Inventors: Gary B. Gordon, Saratoga; Scott A. Conradson, Palo Alto; Kay Lichtenwalter, San Jose, all of Calif.

[73] Assignee: Hewlett-Packard Company, Palo Alto, Calif.

[21] Appl. No.: 337,809

[22] Filed: Nov. 14, 1994

[51] Int. Cl.[6] .................................................. G01N 33/543
[52] U.S. Cl. ........................ 436/518; 432/55; 432/57; 435/287.1; 435/287.2; 435/287.9; 435/288.3; 435/990; 436/524; 436/528; 436/531; 436/532; 436/164; 436/809; 436/800
[58] Field of Search ...................... 422/55, 57; 436/518, 436/524, 528, 531, 532, 164, 809, 800; 435/287.1, 287.2, 287.9, 288.3, 970

[56] References Cited

U.S. PATENT DOCUMENTS 4,748,042  5/1988  Linnecke et al. .................... 422/56
5,073,340 12/1991  Covington et al. .................. 422/57

*Primary Examiner*—Christopher L. Chin

[57] ABSTRACT

An assay system for detecting the binding of a mobile reactant to an immobilized reactant on an assay plate. The assay plate includes a substrate having an assay spot deposited thereon. The assay spot includes the immobilized reactant. In the present invention, a carrier dye is included in the assay spot, the amount of the carrier dye indicating the amount of the immobilized reactant that is present in the assay spot. In the preferred embodiment of the present invention, the assay spot is generated by depositing liquid on the assay plate at a location corresponding to the assay spot. The carrier dye is dissolved in the liquid and remains after the liquid evaporates. The amount of carrier dye in each spot may be measured spectroscopically and provides a means for identifying defective assay plates. The amount of carrier dye in each spot may also be recorded on the assay plate and used in conjunction with measurements of the amount of material bound to the assay spot to determine the concentration of a reactant in a solution being tested for the reactant.

4 Claims, 1 Drawing Sheet

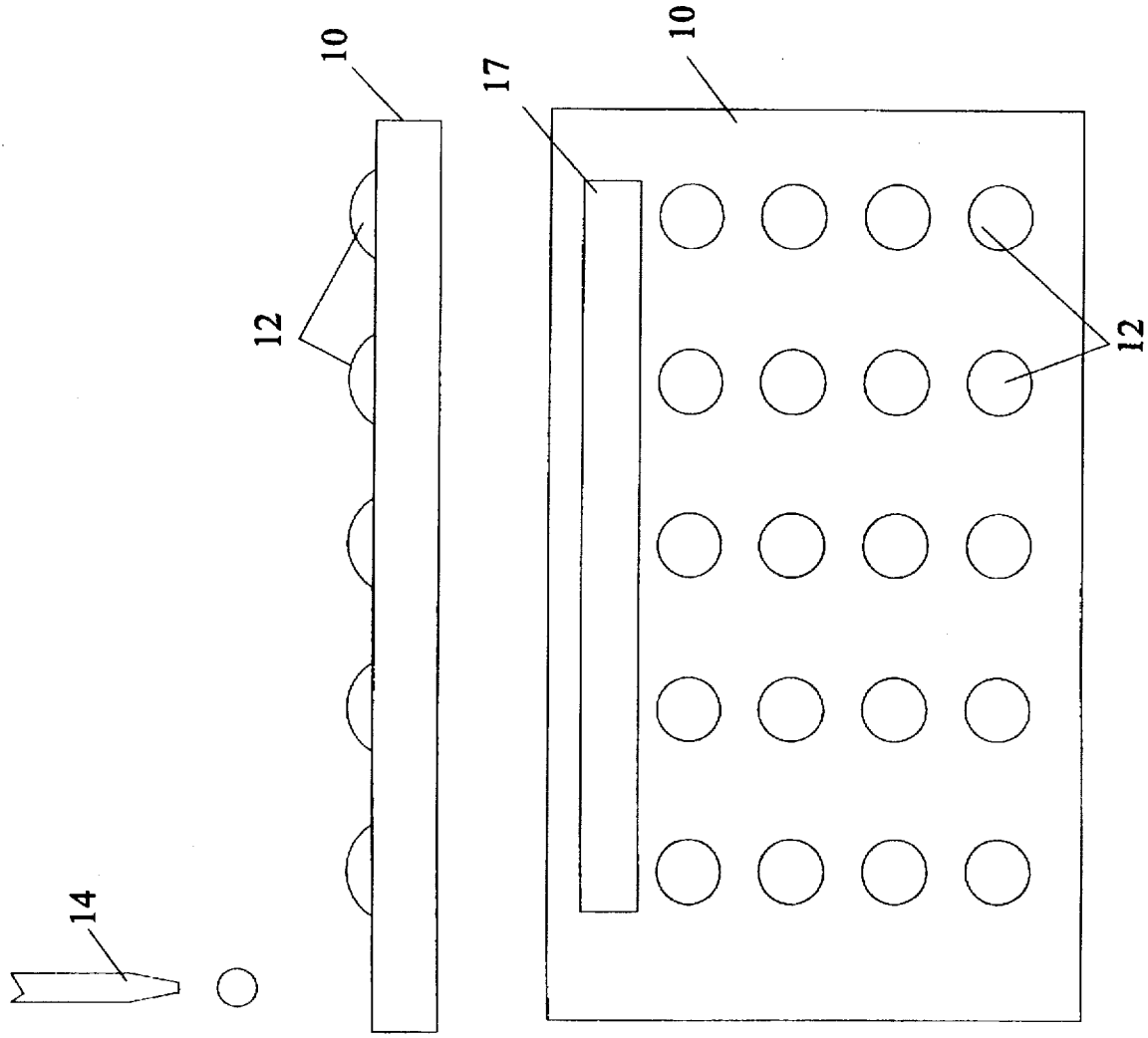

1

BIOCHEMICAL ASSAY PLATE AND METHOD FOR MAKING THE SAME

FIELD OF THE INVENTION

The present invention relates to biochemical assays, and more particularly, to assays in which the presence of a target reactant is determined by measuring the amount of material that is bound to an immobilized reactant.

BACKGROUND OF THE INVENTION

Reactions between biological molecules exhibit an extremely high degree of specificity. It is this specificity that provides a living cell with the ability to carry out thousands of chemical reactions simultaneously in the same "vessel". In general, this specificity arises from the "fit" between two molecules having very complex surface topologies. For example, an antibody binds a molecule displaying an antigen on its surface because the antibody contains a pocket whose shape is the complement of a protruding area on the antigen. This type of specific binding between two molecules forms the basis of numerous biological assays.

For example, the binding between an antibody and molecules displaying a particular antigenic group on their surface may be used as the basis for detecting the presence of the antibody, molecules carrying the antigenic group, or the antigenic group itself. This type of assay forms the basis of numerous medical diagnostic tests. All of these tests depend on detecting and measuring the binding of an antibody molecule that is specific for a particular antigenic group to a molecule carrying the group in question. In general, one of the two molecular species is immobilized on a support surface where it acts as a "glue" for binding the other species. In one class of assays, in which either the antibody or the molecule carrying the antigenic group is to be assayed, one of the two species is covalently immobilized to the support and the other is free in solution. The immobilized species is exposed to the solution that may contain the soluble species and the amount of material bound to the immobilized species after the exposure is measured. In a second class of assays in which the antigenic group itself is to be assayed, one of the two species is covalently immobilized to the support and the other is electrostatically bound to the covalently immobilized species. A solution containing a small molecule having the antigenic group thereon will interfere with the electrostatic binding. This leads to the release of the electrostatically bound species. These assays detect the degree of release of the electrostatically bound species.

Antibodies and antigen carrying molecules are but one of a number of classes of biological molecules whose binding can form the basis of an analytic procedure. For example, nucleic acids are linear polymers in which the linked monomers are chosen from a class of 4 possible sub-units. In addition to being capable of being linked together to form the polymers in question, each unit has a complementary sub-unit to which it can bind electrostatically. For example, in the case of DNA, the polymers are constructed from four bases that are usually denoted by A, T, G, and C. The bases A and T are complementary to one another, and the bases G and C are complementary to one another. Consider two polymers that are aligned with one another. If the sequences in the polymers are such that an A in one chain is always matched to a T in the other chain and a C in one chain is always matched to a G in the other chain, then the two chains will be bound together by the electrostatic forces. Hence, an immobilized chain can be used to bind the complementary chain. This observation forms the basis of tests that detect the presence of DNA or RNA that is complementary to a known DNA or RNA chain. Such detection forms the basis of a number of medical and/or diagnostic tests.

The methods by which the binding of the mobile reactant to the immobilized component of the system is measured varies with the particular reactants. However, a significant fraction of all of the tests involve the measurement of a fluorescent dye that is associated with either the bound or mobile reactant. The dye may be attached to the reactant from the beginning of the process or it may be added through various chemical steps after the mobile and immobilized reactants have been brought into contact with one another.

Systems for medical diagnosis often involve a bank of tests in which each test involves the measurement of the binding of one mobile component to a corresponding immobilized component. To provide inexpensive test kits, systems involving a matrix of immobilized spots has been suggested. Each spot includes the immobilized component of a two component test such as described above. The fluid to be tested is typically brought into contact with the matrix. After chemical processing, the amount of fluorescence associated with each of the spots in the matrix is measured.

The matrix is typically constructed by dispensing small quantities of the immobilized component onto a substrate such as glass or filter paper. For the purposes of the present discussion, the precise form of dispensing apparatus is of little importance. It is sufficient to note that all dispensers have a finite failure rate. When a dispenser fails, the quantity of material deposited on the substrate may be significantly less than or greater than the desired amount. Since the test results are typically based on the assumption that a known amount of material was deposited, such a failure can lead to an erroneous result. In most cases, a dispenser failure will lead to a false negative result, since most dispensing systems fail by clogging, and hence, under dispense.

Many tests require a quantitative result to be properly interpreted. Such tests place an added burden on the dispensing system, since an error in the precise amount of reagent dispensed can lead to erroneous results. Hence, either the amount of material dispensed must be recorded or some quality control procedure must be used to assure that a predetermined amount of material was deposited by the dispenser.

Broadly, it is the object of the present invention to provide an improved method for detecting errors in the dispensing of the reagents in matrices of test such as described above.

It is a further object of the present invention to provide a means for measuring the amount of material actually dispensed in a test matrix so that the test results may be given quantitative significance.

These and other objects of the present invention will become apparent to those skilled in the art from the following detailed description of the invention and the accompanying drawings.

SUMMARY OF THE INVENTION

The present invention is an improved assay system for detecting the binding of a mobile reactant to an immobilized reactant on an assay plate. The assay plate includes a substrate having an assay spot deposited thereon. The assay spot includes the immobilized reactant. In the present invention, a carrier dye is included in the assay spot, the amount of the carrier dye indicating the amount of the immobilized reactant that is present in the assay spot. In the preferred embodiment of the present invention, the assay spot is generated by depositing liquid on the assay plate at a location corresponding to the assay spot. The carrier dye is dissolved in the liquid and remains after the liquid evaporates. The amount of carrier dye in each spot may be measured spectroscopically and provides a means for identifying defective assay plates. The amount of carrier dye in each spot may also be recorded on the assay plate and used in conjunction with measurements of the amount of material bound to the assay spot to determine the concentration of a reactant in a solution being tested for the reactant.

BRIEF DESCRIPTION OF THE DRAWINGS

FIG. 1 is a side view of an assay plate according to the present invention.

FIG. 2 is a top view of the assay plate shown in FIG. 1.

DETAILED DESCRIPTION OF THE INVENTION

The present invention may be more easily understood with reference to FIGS. 1 and 2 which are side and top views of a matrix of test spots 12 deposited on a substrate 10. The individual spots are typically dispensed by a dispensing apparatus 14. Each test spot includes one member of a pair of chemical structures that will bind to one another if brought into contact with one another. The chemical species included in the test spot will be referred to as the immobilized species. The other member of the pair will be referred to as the mobile species.

The immobilized species is typically deposited on substrate 10 in a carrier liquid. In principle, each spot includes a different immobilized species or concentration thereof that will become attached to substrate 10 when the carrier liquid evaporates. One prior art method for preparing assay plates involves coating a glass substrate with an organo-silane having active groups that will covalently bind the immobilized component when the later is dispensed onto the substrate in an appropriate carrier liquid. The presence of a target species is determined by measuring the amount of material bound to the corresponding test spot when a solution to be tested is brought into contact with the test spot. Test plates such as that shown in FIGS. 1 and 2 are designed to test for a plurality of mobile species simultaneously.

It should be noted that the target species may be the mobile species itself or a third species which interferes with the binding of the mobile species to the immobilized species. An inhibition reaction of the type discussed above with respect to antibody-antigen binding assays is an example of the second type of assay.

The manner in which the test spots are generated may be more easily understood with reference to a test spot for detecting a DNA molecule having a specific nucleotide sequence. As noted above, a single stranded DNA molecule will bind to a second single stranded DNA molecule if the second DNA molecule has a sequence that is complementary to the first DNA molecule. The amount of bound DNA may be measured photometrically by measuring the amount of dye present when the bound test spot is treated with a dye that binds to double stranded DNA molecules. Alternatively, the second DNA molecules can be labeled with a dye that can be measured photometrically.

As noted above, dispensing apparatus 14 has a finite error rate. In most test systems, the amount of material in each spot must be controlled to within some predetermined limits to assure that the test based on the spotted material will yield meaningful results. The present invention provides a means of measuring the amount of material deposited on the substrate; and hence, a means of verifying the operation of dispensing apparatus 14. In addition, the present invention provides data that may be used in interpreting the final test results.

In the preferred embodiment of the present invention, the immobilized component is dispensed in a solution that contains a dye, referred to as the carrier dye in the following discussion. The carrier dye provides a means for measuring the amount of immobilized component that was actually delivered. There are three different arrangements for providing the carrier dye. The simplest method involves using a soluble dye that is left behind when the solution used to dispense the immobilized component evaporates. This method may be used in quality control systems to detect assay plates that were improperly made. It may also be used to normalize later test results to the amount of material dispensed provided the amount of carrier dye is determined before treating the assay plate with any solution or chemical that could remove the dye. In this embodiment of the present invention, information specifying the amount of carrier dye must be recorded for each assay plate spot. For example, the amount of dye measured for each spot may be recorded in machine readable form at a predetermined place on the assay plate.

Recording the carrier dye concentration significantly increases the complexity of the assay system, hence the preferred embodiment of the present invention utilizes a method in which the carrier dye is covalently bound to the substrate. As noted above, assay plates are typically fabricated by first coating a glass substrate with an organo-silane compound having active groups. The immobilized compound is modified such it has chemical groups that will bind to the active groups of the organo-silane. The immobilized compound may also be chemically modified to carry the carrier dye. In the case of proteins or DNA, the immobilized compound may be bound through the amino groups that are already in the proteins or additional groups that are added. The resultant covalent attachment of the carrier dye prevents the dye from being washed off during subsequent processing.

An alternative embodiment of the present invention utilizes a carrier dye that binds directly to the organo-silane layer on the glass. In this case, the organo-silane must have two types of active groups, one that binds the dye and one that binds the activated immobilized component.

In either case, once the carrier dye is bound to the substrate either directly or through the immobilized component, the amount of carrier dye can be measured at the same time the final assay is read. The carrier dye concentration measurement must be made at a wavelength that is different from that used to measure the binding of the immobilized component to the mobile component.

Any of the above-described embodiments of the present invention may be used to provide quality control on the assay plate production line. Here, the carrier dye in each spot may be measured before the test plate containing the matrix is shipped. If the measured amount of dye in any spot is outside of the allowed range for that spot, the test plate is rejected and its shipment prevented.

In addition, the results of some tests may depend on a knowledge of the amount of material deposited in the corresponding spots on the test plate. The present invention provides a means for determining the amount of material. As noted above, the amount of material determined during the quality control measurements may be recorded on the plate in a predetermined region of the plate such as region 17 shown in FIG. 2. Alternatively, the amount of material deposited in each spot may be determined during the scanning of the spots at the time the assay dye concentration is measured. Since the preferred embodiment of the present invention uses different dyes for the carrier and assay dyes, a simple two wavelength measurement can provide the data for both dyes.

While the above examples of assays and associated assay plates have been explained in terms of an immobilized reactant that is a single stranded DNA molecule and a mobile reactant that is also a DNA molecule, it will be apparent to those skilled in the art that the present invention may be applied to assays based on a number of different mobile and immobilized reactants. For example, the present invention may be utilized with assays in which the mobile and immobilized reactants are antibodies and molecules, viruses, cells, or other structures displaying antigens bound by the antibodies. In addition, the present invention may be utilized with mobile and immobilized reactant pairs in which one member of the pair is an enzyme and the other is a substrate bound by the enzyme. Similarly, the present invention may be utilized with assays in which one or both members of the pair are RNA molecules.

A number of different dyes are suitable for use with the present invention. Suitable fluorescent dyes include cascade blue (acetylazide), Indo-1, DAPI (4',6-diamidino-2-phenylirdole, HCl), flourescein isothiocyanate, nitrobenzoxadiazole, pyrene, ethidium bromide, and the acridine dyes. These dyes cover a number of different wavelength regions both with respect to excitation and emission wavelengths.

It should also be noted that dyes, other than fluorescent dyes may be used. For example, if the dye can be measured in the visible range, a simple visible inspection of the assay plate can be used to detect plates in which the amount of immobilized reagent dispensed was markedly out of the allowable range. Bromo phenol blue may be used for a dye in the visible range.

Various modifications to the present invention will become apparent to those skilled in the art from the foregoing description and accompanying drawings. Accordingly, the present invention is to be limited solely by the scope of the following claims.

What is claimed is:

1. In an assay system utilizing an assay plate for detecting the binding of a mobile reactant, said assay plate comprising a substrate having an assay spot deposited thereon, said assay spot comprising an immobilized reactant, said immobilized reactant binding said mobile reactant when said mobile and immobilized reactants are brought into contact with one another, the improvement comprising a carrier dye in said assay spot, the amount of said carrier dye indicating the amount of said immobilized reactant that is present in said assay spot.

2. The assay system of claim 1 wherein said carrier dye comprises a fluorescent dye.

3. The assay system of claim 1 further comprising means for recording information indicative of the amount of said carrier dye in said assay spot in response to the measurement of the amount of said carrier dye in said spot.

4. The assay system of claim 1 wherein the amount of said mobile reactant that is bound to said immobilized reactant is measured by detecting the quantity of an assay dye in said assay spot after said mobile reactant is brought into contact with said immobilized reactant and wherein said carrier dye may be spectroscopically distinguished from said assay dye.

* * * * *